United States Patent
Schechter et al.

(10) Patent No.: US 8,455,813 B2
(45) Date of Patent: Jun. 4, 2013

(54) MULTI-PHOTON IONIZATION SPECTROMETER

(75) Inventors: Israel Schechter, Haifa (IL); Valery Bulatov, Nesher (IL)

(73) Assignee: Technion Research and Development Foundation Ltd., Haifa (IL)

(*) Notice: Subject to any disclaimer, the term of this patent is extended or adjusted under 35 U.S.C. 154(b) by 181 days.

(21) Appl. No.: 12/880,179

(22) Filed: Sep. 13, 2010

(65) Prior Publication Data

US 2011/0062321 A1    Mar. 17, 2011

Related U.S. Application Data

(60) Provisional application No. 61/241,907, filed on Sep. 13, 2009.

(51) Int. Cl.
*H01J 27/24* (2006.01)

(52) U.S. Cl.
USPC .................................. 250/282; 250/423 P

(58) Field of Classification Search
USPC ................................. 250/282, 423 P
See application file for complete search history.

(56) References Cited

U.S. PATENT DOCUMENTS

| | | | |
|---|---|---|---|
| 5,757,484 A | 5/1998 | Miles et al. | |
| 2008/0117785 A1 | 5/2008 | Ito et al. | |
| 2008/0245964 A1 | 10/2008 | Miles et al. | |
| 2008/0296485 A1* | 12/2008 | Benter et al. | 250/282 |

OTHER PUBLICATIONS

Ogawa et al., 'Laser Two-Photon Ionization Detection of Aromatic Molecules on a Metal Surface in Ambient Air', Nov. 1, 1992, Analytical Chemistry, vol. 64, No. 21, p. 2615-2617.*

'Laser Mass Spectrometric Analysis of Polycyclic Aromatic Hydrocarbons with Wide Wavelength Range Laser Multiphoton Ionization Spectroscopy', Jul. 1, 1998, Analytical Chemistry, vol. 70, No. 13, p. 2660-2665.*

"Simultaneous Multi-Photon Ionization of Aromatic Molecules in Polymer Solids with Ultrashort Pulsed Lasers"; Guo J. et al.; Chemical Physics Letters, vol. 475, Issue 4-6, Jun. 25, 2009, pp. 240-244.

"Instrumental factors in resonance enhanced multi-photon ionization of FIB-sputtered atoms", Sakamoto T. et al.; Applied Surface Science, vol. 225, Issue 4, Dec. 15, 2008, pp. 1580-1583.

"355 nm multiphoton dissociation and ionization of 2, 5-dihydroxyacetophenone"; Dyakov, Y.A et al.; Journal of Physical Chemistry A vol. 113, Issue 52, Dec. 31, 2010, pp. 14987-14994.

"A desorption mechanism of water following vacuum-ultraviolet irradiation on amorphous solid water at 90 K"; Hama, T et al.; Journal of Chemical Physics, vol. 132, Issue 16, Apr. 28, 2010, Article No. 164508.

(Continued)

*Primary Examiner* — Jack Berman
*Assistant Examiner* — Eliza Osenbaugh-Stewart
(74) *Attorney, Agent, or Firm* — Pearl Cohen Zedek Latzer, LLP

(57) ABSTRACT

A method of assaying a solid or liquid material, the method comprising: illuminating a sample of the material with pulses of light at a plurality of different wavelengths at which atoms and/or molecules in the material are ionized in multiphoton ionization (MPI) process; generating a value responsive to charge produced in the ionization process for each wavelength to provide an MPI spectrum for the material; and processing the MPI spectrum to assay an atom or molecule in the material.

31 Claims, 5 Drawing Sheets

OTHER PUBLICATIONS

"Applications of strong interactions between photons and molecules to analytical sciences"; Yamada, S., Analytical Sciences, vol. 25, Issue 9, Sep. 2009, pp. 1059-1068.

"Resonance-enhanced multiphoton ionization time-of-flight mass spectrometry for detection of nitrogen containing aliphatic and aromatic compounds: Resonance-enhanced multiphoton ionization spectroscopic investigation and on-line analytical application"; Streibel, T. et al., Source: Applied Spectroscopy, vol. 60, No. 1, pp. 72-79, Jan. 2006.

"Highly Sensitive Determination of Aromatic Molecules in the Interface Region of an Oil/ Water System Using Laser Two-Photon Ionization"; Inoue, Takanori et al.; The Japan Society for Analytical Chemistry, vol. 54, No. 6, pp. 467-471, Apr. 2005.

"Laser Two-Photon Ionization of 4,4"-Bis[(2-butyloctyl)oxy-p-quaterphenyl] on a Platinum Surface in Ambient Air: Highly Sensitive Detection of Surface Molecules"; Ogawa, Teiichiro et al.; Analytical Sciences, Feb. 1992, vol. 8, pp. 81-82.

"Highly Sensitive Detection of Pyrene by Laser Multi-Photon Ionization on the Surface of Water"; Masuda, Kazuhiro; Analytical Sciences, Apr. 1993, vol. 9, pp. 297-298.

"Application of Laser Multi-Photon Ionization Detection to Thin-Layer Chromatographic Plates"; Kawazumi, H.; Analytical Sciences, Apr. 1993, vol. 9, pp. 309-310.

"A Renewable Liquid Droplet Method for online pollution analysis by Multi-Photon Ionization"; Gridin, Vladimir et al.; Anal. Chem. 1997, vol. 69, pp. 2098-2102.

"Laser Two-Photon Ionization of Pyrene on Contaminated Soils"; Gridin, Vladimr; Anal.Chem. 1996, vol. 68, pp. 3359-3363.

"Particulate Material Analysis by a Laser Ionization Fast Conductivity Method Water Content Effects"; Gridin, Vladimir, Anal.Chem. 1997, vol. 69, pp. 478-484.

"Simultaneous Laser-Induced Multiphoton Ionization and Fluorescence for Analysis of Polycyclic Aromatic Hydrocarbons"; Inoue, Takanori; Anal. Chem. 1998, vol. 70, pp. 4333-4338.

"Determination of Aqueous Solubility and Surface Adsorption of Polycyclic Aromatic Hydrocarbons by Laser Multiphoton Ionization"; Gridin, Vladimir; Anal. Chem.1998, vol. 70, pp. 2685-2692.

"Multiphoton Ionization Spectroscopy as a Diagnostic Technique of Surfaces Under Ambient Conditions"; Chen, Yuheng et al.; Anal. Chem. 2010, vol. 82, pp. 3454-3456.

Willey Online Library: Kirk-Othmer Encyclopedia of Chemical Technology,John Wiley & Sons, Inc.; Published online Jun. 16, 2006; pp. 5-6, 17-18.

J. Garcia Sole et al.; "An Introduction to the Optical Spectroscopy of Inorganic Solids", John Wiley & Sons, Ltd, 2005, pp. 5, 11.

"Applied Spectrography: a compact reference for practitioners"; edited by Jerry Workman, Jr. et al., Academic Press, 1997, pp. 67-73, 193-245.

"Encyclopedia of Analytical Chemistry"; Edited by R.A. Meyers, Wiley, 2001, pp. 1-24.

"Encyclopedia of Analytical Science"; edited by Paul Worsfold et al., AP, 2005, pp. 358-383.

"Handbook of Spectroscopy"; edited by G. Gauglitz et al., Wiley-VCH, 2003, pp. 125-135.

* cited by examiner

US 8,455,813 B2

MULTI-PHOTON IONIZATION SPECTROMETER

CROSS-REFERENCES TO RELATED APPLICATIONS

The present application claims benefit under 35 U.S.C. §119 (e) of U.S. Provisional Application 61/241,907 filed Sep. 13, 2009, the entire content of which is incorporated herein by reference

TECHNICAL FIELD

Embodiments of the invention relate to apparatus and methods for nondestructive assaying components of a solid material.

BACKGROUND

Absorption spectroscopy methods are methods for assaying components of a material responsive to absorption of electromagnetic radiation by the material. Common to practice of many of the methods, a material to be assayed is exposed to electromagnetic radiation at a plurality of different wavelengths of the radiation. At each wavelength, absorption of the radiation is directly or indirectly measured to determine its absorption by the material as a function of wavelength. The absorption of the electromagnetic radiation as a function of wavelength is referred to as an "absorption spectrum" for the material.

The absorption spectrum comprises contributions from absorption spectra of atoms and molecules that the material contains, each of which has its own unique absorption spectrum. The absorption spectrum for the material is processed to identify absorption spectra of atoms or molecules that contribute to the material's absorption spectrum, and amounts by which they contribute to the absorption spectrum. The identified spectra and amounts are used to identify and assay atoms and molecules that the material comprises.

Absorption spectroscopy is typically used to assay materials in a gaseous state. Absorption spectroscopy of solids in their naturally occurring states under ambient conditions of atmosphere and temperature generally suffers from spectral line broadening that makes it complicated and difficult to use absorption spectroscopy to assay components of the solids or liquids. A spectral line of an atom or molecule marks a generally narrow band of wavelengths (or frequencies) in the electromagnetic spectrum associated with a difference between two different energy states of the atom or molecule at which it absorbs or emits energy. Every atom or molecule has its own unique family of spectral lines. The family of spectral lines, defines, the atom's or molecule's emission and absorption spectrum. When referring to absorption of electromagnetic energy by the atom or molecule, the family of spectral lines is referred to as the atom's or molecule's absorption spectrum. Broadening of a spectral line of an atom or molecule refers to an increase, a "broadening", of the range of energies, and therefore of wavelength band, at which the atom or molecule can absorb energy to make a transition been energy states associated with the spectral line.

Spectral line broadening of an atom or molecule in a solid is generated not only in accordance with the Heisenberg uncertainty principle, which puts a lower limit on a spectral line width associated with a given state transition of an atom or molecule. Interaction of the atom or molecule with other components of the densely packed material characteristic of the solid, and Doppler shifts due to random thermal motion of the atom or molecule contribute to its spectral line broadening.

Spectral line broadening in a solid or liquid in a natural state and under ambient conditions is typically so large that spectral lines of different atoms and/or molecules in the solid tend to overlap substantially. It is therefore difficult, if at all practically possible, to identify an atom or molecule in a solid or liquid from an absorption spectrum acquired for the solid or liquid in its natural state and under ambient atmospheric and temperature conditions. As a result, absorption spectroscopy assaying of solids and liquid performed under ambient conditions has not generally been useful.

SUMMARY

An embodiment of the invention provides apparatus, hereinafter referred to as a multi-photon ionization (MPI) spectrometer, and methods for acquiring an absorption spectrum for a solid or liquid under ambient conditions responsive to a multi-photon ionization (MPI) process, and assaying components of the solid responsive to the absorption spectrum.

An MPI process is a process in which a plurality of photons interacts with an atom or molecule, hereinafter generically referred to as a molecule, to ionize the molecule. By way of example, in a two photon MPI process, a first photon raises an electron in a molecule to an excited state, and a second photon interacts with the molecule before the excited state decays, to add sufficient energy to the electron to free it from, and ionize the molecule. In some MPI processes both photons simultaneously interact with the molecule to free an electron from and ionize the molecule. In an MPI process involving more than two photons, at least two photons interact with a molecule to either raise an electron to an excited state or free the excited electron.

In an embodiment of the invention, an MPI spectrometer comprises a tunable laser and a controller that controls the laser to illuminate a region of a solid being assayed by the MPI spectrometer with pulses of laser light at a plurality of different wavelengths at which light is absorbed by the solid and ionizes material in the solid by MPI processes. At each wavelength, the MPI spectrometer measures current generated by charges produced by the MPI processes to provide a measure of the absorption of light by the solid as a function of wavelength. The absorption of light by MPI processes as a function of wavelength provided by the MPI spectrometer is referred to hereinafter as an "MPI spectrum" of the solid.

Different molecules comprised in the solid have their own distinctive MPI spectra, which contribute to the MPI spectrum acquired for the solid by the MPI spectrometer in accordance with an embodiment of the invention. The acquired MPI spectrum exhibits a relatively dense population of wavelength resolved features. The features are used to identify an MPI spectrum of a molecule in the solid that contributes to the solid's MPI spectrum, and to determine concentration of the molecule in the solid.

In accordance with an embodiment of the invention, the MPI spectrometer provides current measurements by integrating current for each pulse provided by the laser during an integration period following transmission of the pulse. Duration and timing of the integration period following transmission of a pulse are determined to provide an acceptable signal to noise ratio (SNR) for the integrated current measurements. Build up of a space charge field in the MPI spectrometer that might interfere with current measurements is moderated by providing sufficient drainage of positive charge produced by the ionization process that accumulates in the solid. Intensity of light in the pulses is monitored and adjusted to moderate intensity changes that might bias and introduce errors in the current measurements and thereby in the MPI spectrum of the solid.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

Figure 1:
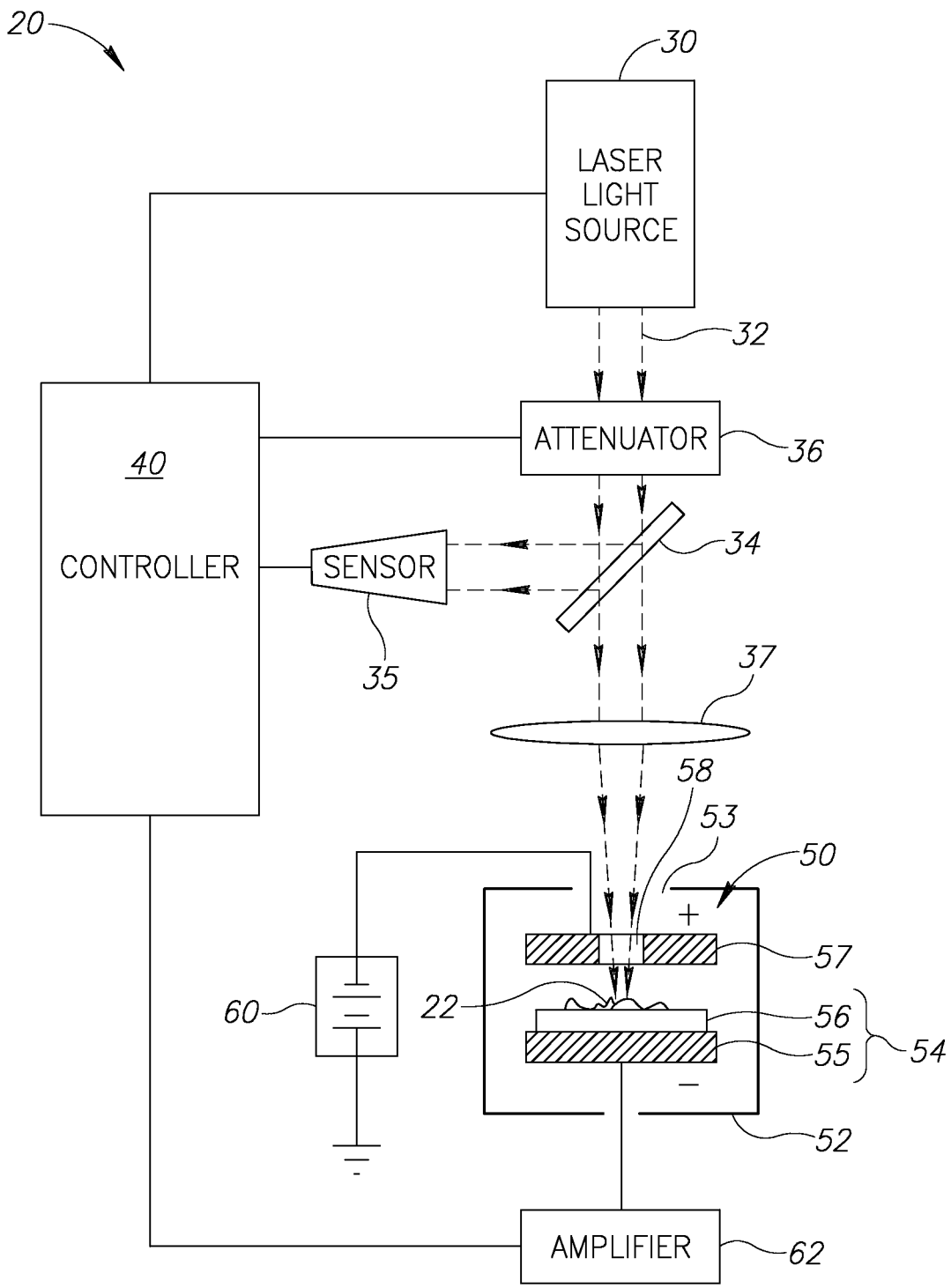
FIG. 1 schematically shows an MPI spectrometer assaying a solid material in accordance with an embodiment of the invention.
Figure 2:
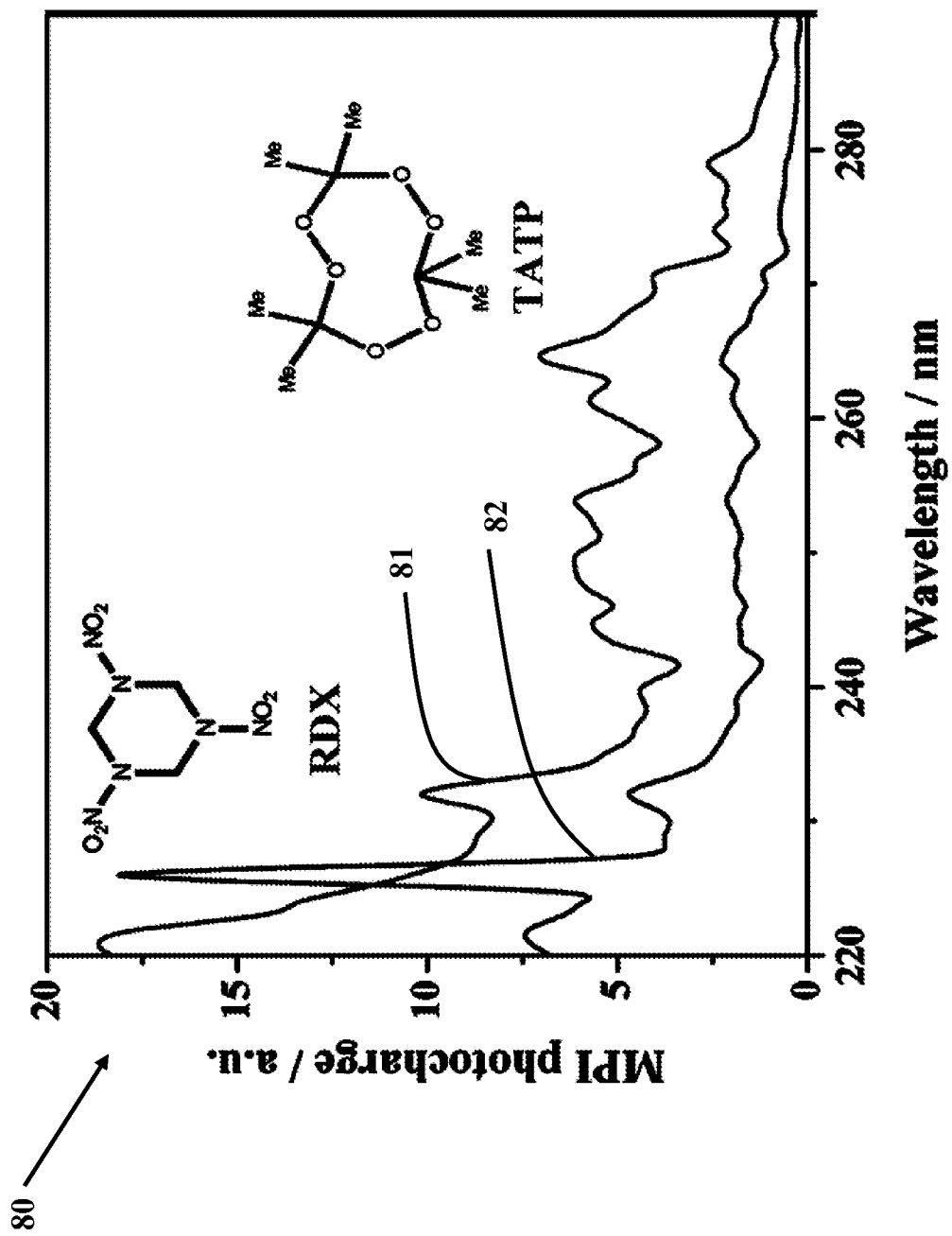
FIG. 2 shows MPI spectra for the explosives RDX and TATP acquired using an MPI spectrometer, in accordance with an embodiment of the invention.
Figure 3A:
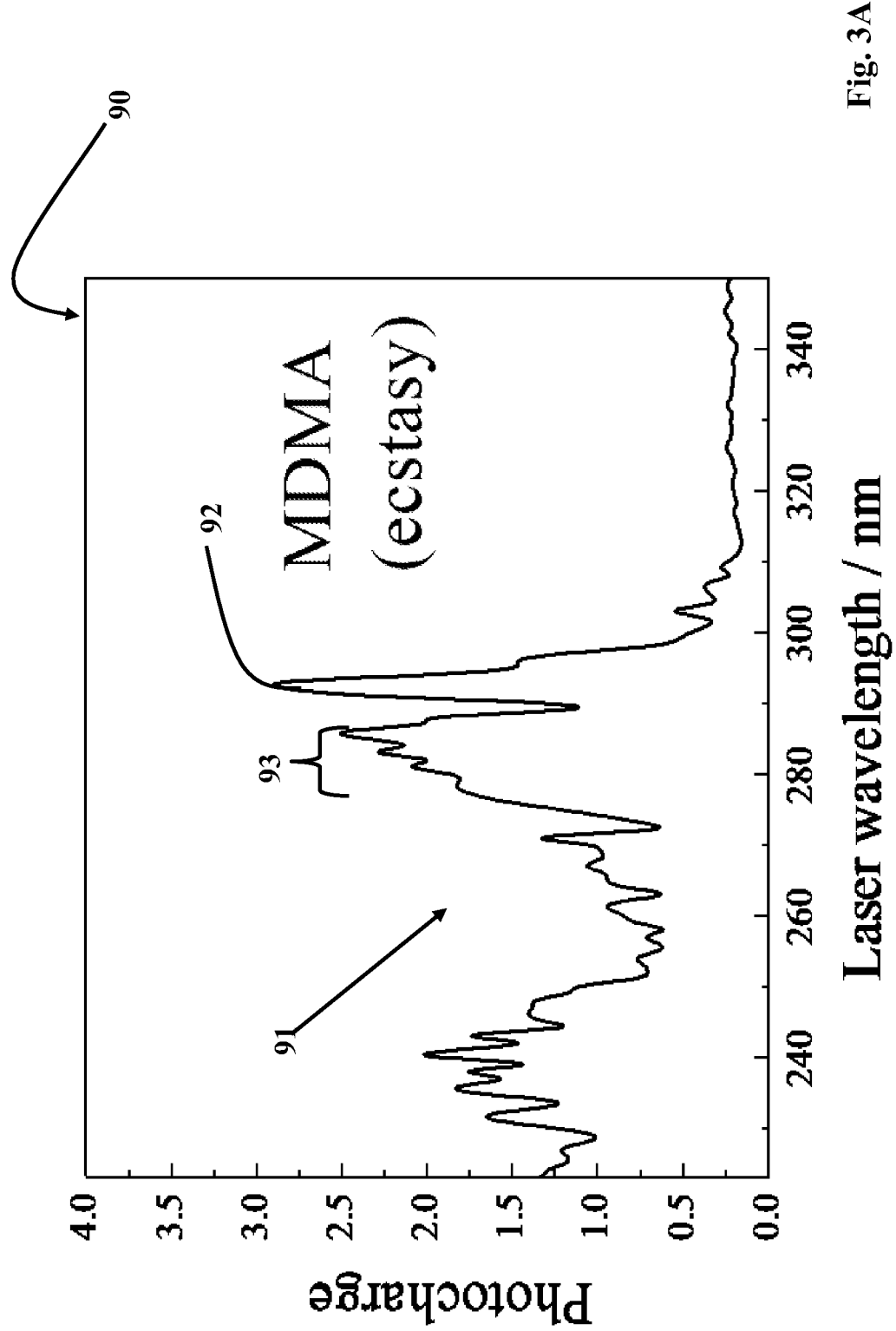
FIG. 3A shows an MPI spectrum for the MDMA (ectasy) molecule acquired using an MPI spectrometer, in accordance with an embodiment of the invention.
Figure 3B:
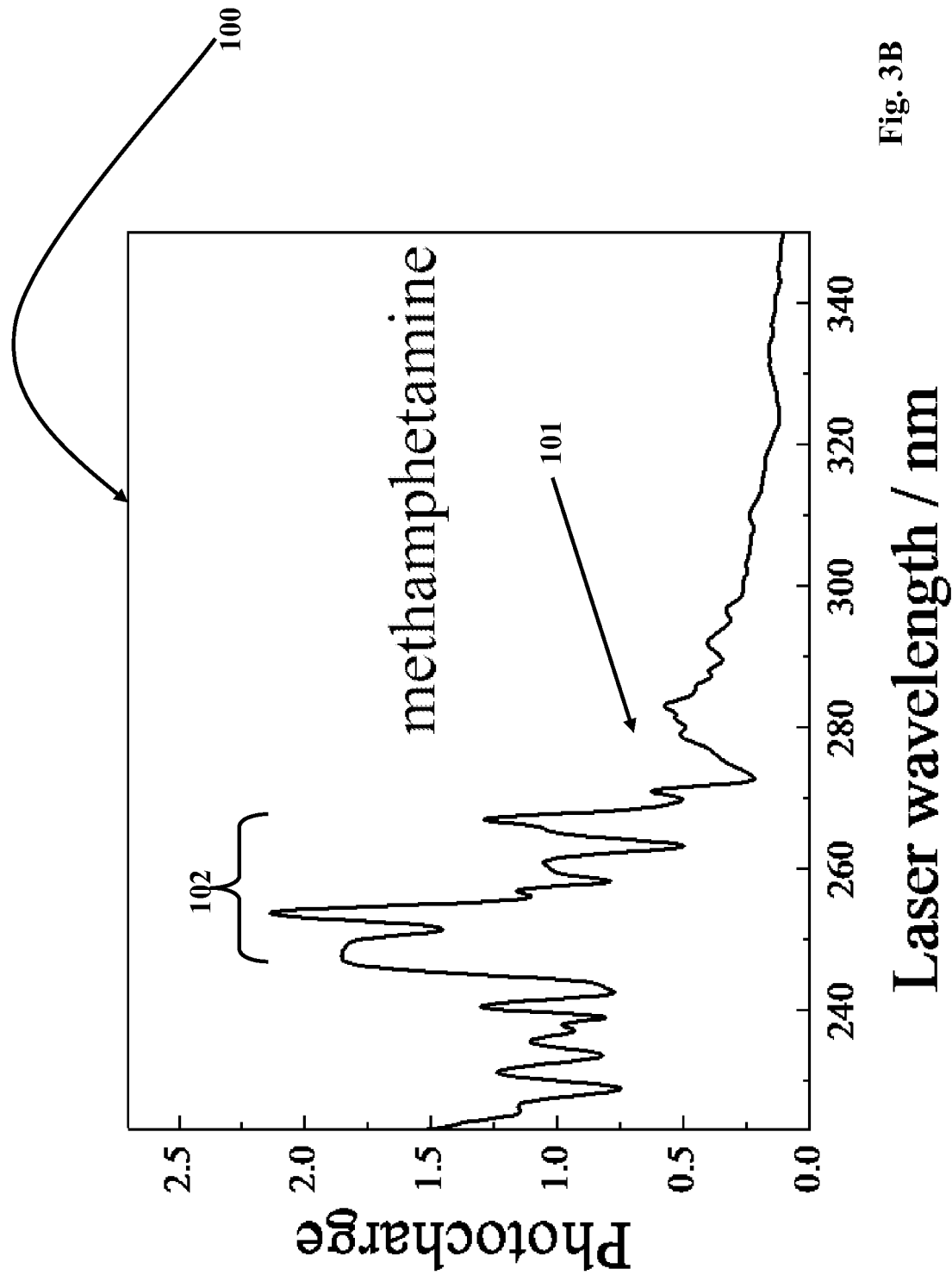
FIG. 3B shows an MPI spectrum for the methamphetamine molecule acquired using an MPI spectrometer, in accordance with an embodiment of the invention.
Figure 3C:
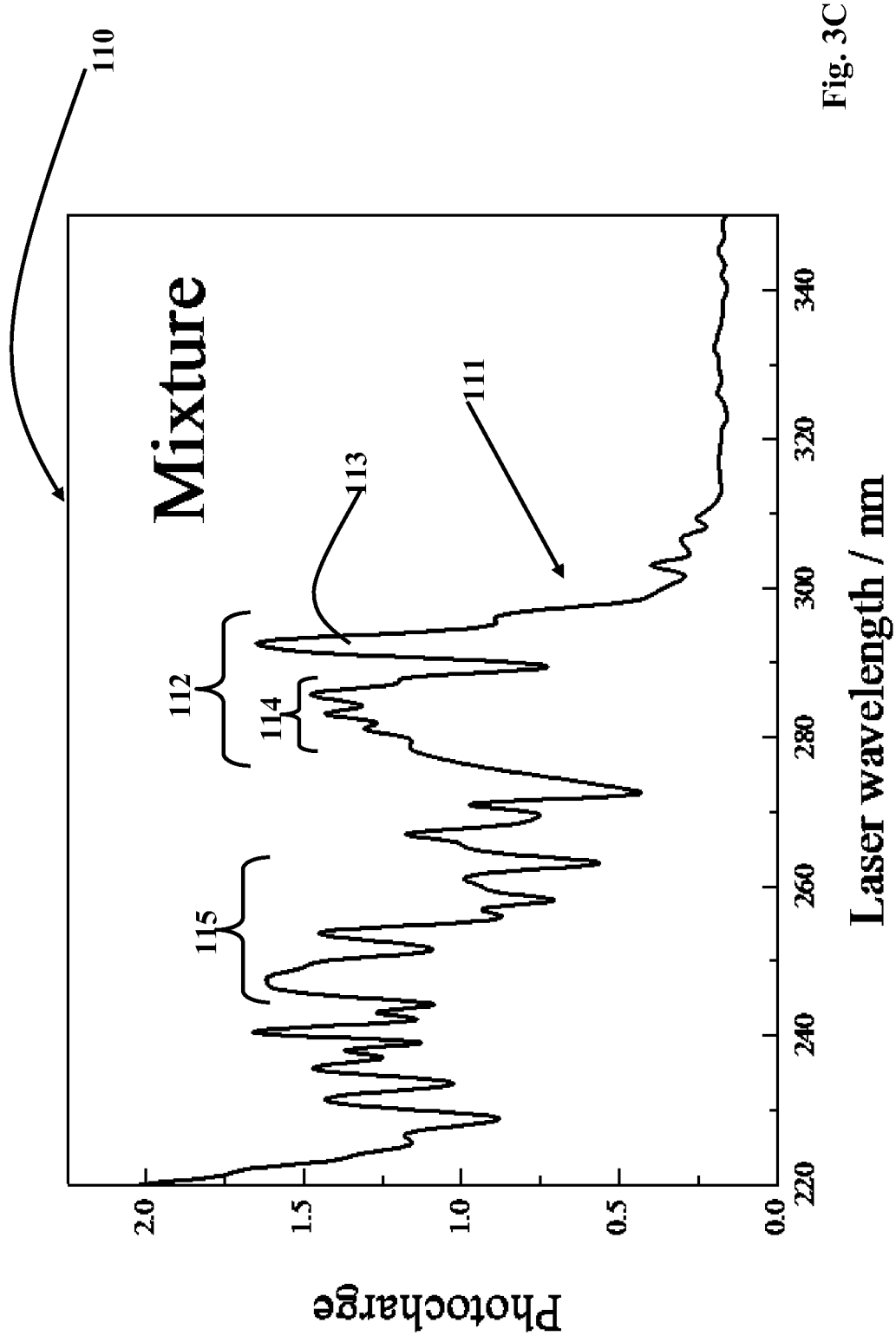
FIG. 3C shows a simulated MPI spectrum acquirable for a mixture comprising MDMA and methamphetamine using an MPI spectrometer, in accordance with an embodiment of the invention.

In the following, a general description of an MPI spectrometer in accordance with an embodiment of the invention is given with reference to FIG. 1. An exemplary numerical specification of an embodiment of the invention having a configuration similar to that shown in FIG. 1 is then provided. MPI spectra for the explosives RDX and TATP acquired under ambient atmospheric and temperature conditions using an MPI spectrometer in accordance with an embodiment of the invention are presented in FIG. 2, FIG. 3A and FIG. 3B show MPI spectra acquired respectively for the psychedelic molecules MDMA (ecstasy) and methamphetamine using an MPI spectrometer in accordance with an embodiment of the invention. FIG. 3C is a simulation of an MPI spectrum generated by a computer for a mixture of ecstasy and methamphetamine. Comparison of the spectrum in FIG. 3C with the spectra in FIGS. 3A and 3B indicates that an MPI spectrum acquired by an MPI spectrometer in accordance with an embodiment of the invention for a solid material comprising the psychedelic molecules could be processed to quantitatively assay their presence in the material.

FIG. 1 schematically shows a multi-photon ionization (MPI) spectrometer 20 assaying a sample of a solid material 22, hereinafter also referred to as a "target 22" or "target material 22", in accordance with an embodiment of the invention.

MPI spectrometer 20 comprises a tunable laser light source 30 controllable by a controller 40 to provide light, represented by dashed, arrowed lines 32, at a plurality of different wavelengths in a range of wavelengths at which light ionizes material in target 22 by MPI processes.

Target 22 is held, optionally under ambient atmospheric conditions of temperature and pressure, by a target holder 50 housed in a Faraday cage 52 formed having an aperture 53 through which light 30 from laser light source 30 passes to illuminate the target. Target holder 50 optionally comprises a support platform 54 having a first electrode 55 and optionally a support plate 56 that rests on the first electrode and on which target 22 is positioned. A second electrode 57 is displaced from and located over support plate 56 and is formed so that it does not prevent light 32 from laser light source 30 from illuminating target 22. Optionally, second electrode 57 is formed having an aperture 58 through which light passes to illuminate the solid. In some embodiments of the invention, second electrode 57 comprises a mesh electrode. In some embodiments, second electrode 57 is formed from a suitable conducting material, such as a polycrystalline or amorphous semiconductor oxide, by way of example ZnO, $In_2O_3$ and/or $SnO_2$ that is transparent to light 30.

In some embodiments, electrode 57 is formed having a needle shape and, optionally, is moveable relative to the target 22 so that its needle point can be positioned at different locations over the target. By moving the needle electrode to different locations relative to the target 22, MPI spectrometer can spatially scan the target and acquire MPI spectra for different regions of the target.

Intensity of light from laser light source 30 that illuminates target 22 is optionally monitored by a beam splitter 34 and an optical sensor 35. Beam splitter 34 directs a portion of light 30 provided by the laser light source to sensor 35. Sensor 35 generates signals responsive to intensity of the light it receives from the beam splitter and transmits the signals to controller 40. Controller 40 controls an attenuator 36 responsive to the received signals to control intensity of light from laser light source 30 that illuminates target 22. Light that passes through beam splitter 34 is focused on target 22 by a suitable optical system, schematically represented by, and referred to, as a lens 37.

A power supply 60 maintains second electrode 57, hereinafter also referred to as anode 57, at a positive potential relative to first electrode 55, hereinafter also referred to as cathode 55, and generates an electric field in the space between them. Cathode 55 is connected to a current amplifier 62 that senses and amplifies current flowing between the cathode and the anode, and inputs the amplified current to controller 40.

In accordance with an embodiment of the invention, controller 40 controls laser light source 30 to illuminate a region of target 22 with a plurality of pulses of light 32 for each of a plurality of different wavelengths at which light ionizes material in the solid by an MPI process. Light 32 from each pulse at each wavelength is absorbed by and ionizes molecules in the target in an MPI process, freeing electrons from the molecules and ejecting them from the target. The ejected electrons are accelerated toward anode 57 by the potential difference generated by power supply 60 between the anode and cathode 55 and drift to, and are collected by, the anode. The drifting electrons produce a current between the anode and cathode, which is sensed and amplified by amplifier 62 and input to controller 40.

For each light pulse at a given wavelength, the amplified current is integrated by controller 40 during an integration period between first and second, respectively "start" and "stop", times to accumulate a charge, hereinafter an "MPI charge". The MPI charge is a measure of a total number of electrons produced by the MPI process engendered by light 32 at the given wavelength from the light pulse and therefore of absorption of light by the target at the given wavelength.

In an embodiment of the invention, the MPI charges acquired for the plurality of light pulses that illuminate the target with light 32 at a given wavelength are averaged and normalized to an average energy per pulse incident on the target to provide a measurement of the absorption of light 32 by the target at the wavelength. The plurality of absorption measurements acquired at the different wavelengths at which MPI spectrometer 20 illuminates target 22 provide an MPI spectrum for the target. In an embodiment of the invention, MPI spectrometer 20 comprises a processor (not shown) that processes the MPI spectrum to assay a component or components of the target that contribute to the MPI spectrum. The processor may be housed separately from other components of the controller.

Any of various methods may be used to determine components that contribute to an MPI spectrum in accordance with an embodiment of the invention. Optionally, controller 40 comprises a look up table (LUT) of MPI spectra of atoms and molecules that may contribute to MPI spectra of target materials assayed by the MPI spectrometer. Any of various multivariate analysis or pattern recognition algorithms may be used to determine how much each of a plurality of the LUT MPI spectra contributes to an MPI spectrum of a given target material. The determined amounts of the contributions are used to provide an assay of the target material.

For example, in an embodiment of the invention, a given MPI spectrum acquired by MPI spectrometer 20 is assumed to be a linear combination of component MPI spectra archived in the LUT. Coefficients of the component spectra are determined optionally by a least squares fit. The coefficients are used to determine concentrations in the target material of molecules associated with the component spectra.

It is noted that in the discussion above, pulses of laser light 32 are described as characterized by light at a single wavelength. In some embodiments of the invention, laser light 32 comprises light at a first wavelength chosen to excite an electron of a particular molecule from a given first energy state to a given second, excited energy state, and light at a second wavelength chosen to add a given amount of energy to the excited electron to free it from the molecule. Optionally, the second wavelength is chosen so that the light adds a minimum amount of energy needed to free the electron from the second, excited, state and ionize the molecule. By configuring light 32 to comprise light at wavelengths that "pick out" and excite particular excited energy states of a molecule and add minimum amounts of energy to free electrons from the particular excited states, MPI 20 can acquire MPI spectra having enhanced specificity for the molecule.

In an example of an embodiment of the invention, laser light source 30 comprises an optical parametric oscillator (OPO) pumped by a frequency doubled third harmonic of a Nd:YAG laser (355 nm). Lens 37 is optionally a quartz lens having a focal length of 20 cm located about 10 cm from support plate 56. Anode 57 and cathode 55 are separated by about 10 mm, and power supply 60 maintains a potential difference of about 2 kV between the electrodes. Current amplifier 62, optionally a Keithley 428 amplifier, operates with a response time between about 1 microsecond and about 3 microseconds at a gain of between about $10^6$ volts per ampere (V/A) to about $10^7$ V/A.

To provide an MPI spectrum having density of features advantageous for resolving different molecules in a target material 22, controller 40 controls laser light source 30 to illuminate the target with a plurality of pulses of light at each of a plurality wavelengths spaced every 0.1 nanometers (nm) in a range of wavelengths from about 220 nm to about 355 nm. In an embodiment of the invention, the number of the plurality of pulses is greater than 10. In some embodiments of the invention, the number of the plurality is greater than 20. Optionally, the number is greater than 50. Optionally, the widths of the pulses are equal to or less than about 5 ns. Optionally, the pulse widths are less than or equal to about 1 ns. In some embodiments of the invention, pulse widths are less than 500 picoseconds (ps). Optionally the pulse width is equal to about 10 ps. Controller 40 controls intensity of light 32 provided by laser light source 30 so that from pulse to pulse, intensity varies less than a predetermined amount from a normative intensity. Optionally, the controller controls intensity of light 32 so that the pulse to pulse intensity variance is less than 10% of the normative intensity. In an embodiment of the invention, the normative intensity for 5 ns pulse widths is determined to be an intensity for which a pulse of laser light 30 imaged by lens 37 on target 22 delivers between about 1 Joule/cm$^2$ (J/cm$^2$) and about 2 J/cm$^2$ to the target.

Ionization of, and removal of electrons from, target 22 by the MPI processes engendered by the light pulses provided by laser light source 30, leaves positive ions in the target material. To maintain current of the freed electrons from cathode 55 to anode 57, and prevent buildup of positive charge in the target from reducing or stopping the current, accumulated positive charge is neutralized by flow of electrons from the cathode into target material 22.

In an embodiment of the invention, support plate 56 is configured to provide sufficient conductivity by contact with target material 22 to support a satisfactory flow of electrons from the cathode to the target material. However, the support plate advantageously not only provides appropriate conductivity, but is formed so that light 30 does not ionize material in the support plate and thereby generate electrons which might contaminate the electron current generated by MPI processes that is used to determine an MPI spectrum for the target.

In some embodiments of the invention, support plate 56 is conductive and contact of target material 22 with the support plate enables flow of electrons into the target. For wavelengths of light pulses greater than 270 nm, support plate 56 is advantageously formed from platinum (Pt). Platinum has a relatively high ionization potential and light at wavelengths greater than 270 nm does not ionize platinum. It is noted that for MPI spectrometer 20 in which the support plate 56 is formed from a conductive material such as Pt, the support plate and cathode 55 may of course be one and the same, with support plate 56 also functioning as the cathode.

For wavelengths of light 32 in light pulses provided by laser light source 30 between 220 nm and about 270 nm, support plate 56 is optionally formed from quartz. Quartz has a relatively high ionization potential equal to 10.2 electron volts (ev), that is substantially higher than the 5.64 ev energy of a photon having wavelength 220 nm, which is a highest energy photon in the range 220-270 nm. As a result, light 32 does not ionize the quartz, and generate photoelectrons therefrom that might contaminate measurements of current generated by an MPI process of the light with target material 22.

However, quartz is an insulator and does not on its own support current to target material 22. Current for neutralizing positive charge buildup in the material is mediated by a thin layer of water that under ambient conditions adheres to surfaces of quartz. The effectiveness of a support plate 56 formed from quartz in providing conductive contact of target material 22 to cathode 55 is a function of geometry and dimensions of the support plate. Advantageously, quartz support plate 56 is disc shaped and has a thickness equal to between about 0.5 mm and about 1.5 mm and a radius between about 5 mm and about 15 mm. Optionally, the thickness is between about 0.7 mm and about 1.3 mm. In an embodiment of the invention, thickness is equal to about 1 mm. Optionally, the radius is between about 8 mm and about 12 mm. In an embodiment of the invention thickness is equal to about 10 mm.

In an embodiment of the invention, integration start and stop times are determined responsive to current between the cathode 55 and anode 57 as a function of time. Generally, in the first 5 microseconds following transmission of a laser light pulse by laser light source 30 to illuminate target 22, the current exhibits transients, which appear to be caused by displacement currents and laser noise. Therefore, an integration start time in accordance with an embodiment of the invention, is advantageously a time later than 5 microseconds following radiation of the pulse.

In a normal atmosphere, current generated between cathode 55 and anode 57 by electrons released from target 22 by MPI processes is produced by drift of most of the electrons, hereinafter "free electrons", towards the anode, and by drift of oxygen molecules that have captured some of the electrons toward the anode. The free electrons have a much higher drift velocity in the field between the cathode and anode generated by power supply 60 than do the charged oxygen molecules. Therefore, following the period in which strong transients are exhibited, the current as a function of time exhibits a first period having duration of about 5 microseconds in which the current is relatively strong and dominated by drift of free electrons. The first period is followed by an extended second period during which the current is due to the slower drifting charged oxygen molecules and decays. As the current decays, a signal to noise ratio (SNR) for signals produced by amplifier 62 responsive to the current decreases. An integration stop time in accordance with an embodiment of the invention is determined as a time at which the SNR for the amplifier signals decreases to a value less than or about equal to a predetermined SNR. In an embodiment of the invention, the predetermined SNR is equal to 10. Optionally, the predetermined SNR is equal to 8. Optionally, the predetermined SNR is equal to 6. For the configuration of MPI spectrometer given above, the SNR decreases to about 6 at about 200 microseconds following the start time.

It is noted that in a dry nitrogen atmosphere in which there are no, or very little, oxygen molecules, current between cathode 55 and anode 57 is due almost entirely to fast drifting free electrons. There is no current due to slow drifting charged oxygen molecules, and a stop time is advantageously a time equal to about 5 microseconds following the start time, resulting in very short integration times relative to integrations times noted above (200 microseconds) for use of MPI spectrometer 20 in ambient air. The shorter integration times allow for acquiring an MPI measurement at each wavelength by exposing target 22 to many more pulses of light 32 than is generally convenient when operating MPI spectrometer 20 in ambient air. The increased number of light pulses provides an improved SNR for the measurements.

FIG. 2 shows a graph 80 of MPI spectrum 81 and 82 for the explosives RDX and TATP respectively, acquired under ambient conditions by an MPI spectrometer similar to MPI spectrometer 20 shown in FIG. 1. The abscissa of the graph shows wavelength scaled in nanometers. The ordinate shows MPI charge accumulated for each wavelength in arbitrary units. The spectrometer specification was similar to that described above for the exemplary embodiment and operated with 5 ns pulses. Spectra 81 and 82 are useable to detect presence of RDX and TATP in quantities as small as small as a few picomoles at 95% confidence level.

MPI spectra for other explosives, such as HMX, TEN and TNT, drugs such as MDA (3,4-Methylenedioxyamphetamine) and THC (Tetrahydrocannabinol), and various polycyclic aromatic hydrocarbons (PAHs), such as melamine, anthracene and chrysene, were acquired using an MPI spectrometer in accordance with an embodiment of the invention, and similarly indicated detection sensitivities of a few picomoles at 95% confidence level.

FIG. 3A shows a graph 90 of an MPI spectrum 91 acquired for the psychedelic molecule MDMA (ecstasy). The MPI spectrum exhibits a exhibits a relatively rich structure of peaks and valleys unique to ecstasy dominated by a relatively large prong 92 at a wavelength of about 294 nm and a cascade 93 of three peaks to the left of the prong.

FIG. 3B shows a graph 100 of an MPI spectrum 101 acquired for the psychedelic molecule methamphetamine. The MPI spectrum exhibits a defining structure 102 of peaks and valleys in a wavelength region from about 244 nm to about 264 nm.

FIG. 3C shows a graph 110 of a simulated MPI spectrum 111 generated by a computer for a mixture of ecstasy and methamphetamine. A region 112 of MPI spectrum 111 exhibits a large prong 113 at 294 nm and a cascade 114 of three peaks having strong resemblance to respectively large prong 92 at 294 nm and cascade 93 of three peaks in MPI spectrum 90 shown in FIG. 3A for ecstasy. Region 112 is identifiable with ecstasy and indicates the presence of ecstasy in the mixture. A region 115 of MPI spectrum 111 for the mixture between 244 nm and 264 nm bears strong resemblance to structure 102 of peaks and valleys in a wavelength region from about 244 nm to about 264 nm in MPI spectrum 100 for methamphetamine. Region 115 is identifiable with methamphetamine and indicates the presence of methamphetamine in the mixture.

The structure of MPI spectrum 110 and its readily identifiable ecstasy and methamphetamine MPI spectra, indicate that an MPI spectrum acquired by an MPI spectrometer in accordance with an embodiment of the invention for a solid material comprising a mixture of the psychedelic molecules may be processed to quantitatively assay their presence in the material. However, practice of an embodiment of the invention is of course not limited to assaying ecstasy and methamphetamine or mixtures comprising two components. MPI spectrometers and methods may be used in general to assay multi-component solids and liquids.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A spectrometer for assaying a solid or liquid material, the spectrometer comprising:

a laser light source controllable to provide light pulses at a plurality of different wavelengths;

a controller to control the light source so as to illuminate the material with pulses of light at a plurality of different wavelengths to ionize atoms and/or molecules in the material by a multiphoton ionization process (MPI);

a sensor to measure values corresponding to charges generated in the multiphoton ionization process for each of the different wavelengths to acquire an MPI spectrum for the material; and a processor to assay an atom or molecule in the material based on the MPI spectrum.

2. A spectrometer according to claim 1 wherein the controller controls the light source so that a light pulse comprises light at wavelengths tuned to ionize an atom or molecule that might be present in the material by the MPI process by causing transitions between particular energy states of the atom or molecule.

3. A spectrometer according to claim 2 wherein the light at the tuned wavelength comprises light at a first wavelength chosen to excite an electron of the atom or molecule from a given first energy state to a given second, excited, energy state, and light at a second wavelength chosen to add a given amount of energy to the excited electron to free it from the molecule.

4. A spectrometer according to claim 3 wherein the light at the second wavelength is chosen so that the light adds a minimum amount of energy needed to free the electron from the second, excited, state and ionize the molecule.

5. A spectrometer according to claim 1 and comprising a power supply that produces an electric field which operates on charge produced by the MPI process to generate current.

6. A spectrometer according to claim 5 and comprising a current integrator that integrates the current produced at each of the plurality of wavelengths to provide a value for the MPI spectrum at the wavelength.

7. A spectrometer according to claim 6 wherein the current integrator integrates current generated responsive to charge produced by each light pulse from a start time to a stop time following a time at which the light pulse is transmitted to illuminate the material.

8. A spectrometer according to claim 7 wherein the start time is a time at least 5 microseconds following transmission of the light pulse.

9. A spectrometer according to claim 7 wherein the stop time is a time at which a signal to noise ratio (SNR) for current being integrated decreases to a value less than a predetermined SNR.

10. A spectrometer according to claim 9 wherein the predetermined SNR is equal to about 10.

11. A spectrometer according to claim 5 and comprising an electrode connected to the power supply on which the solid or liquid material is positioned.

12. A spectrometer according to claim 5 and comprising an insulating support plate on which the solid or liquid material is positioned.

13. A spectrometer according to claim 12 wherein the support plated is formed from quartz.

14. A spectrometer according to claim 13 wherein the support plate has a thickness between about 0.5 mm and about 1.5 mm.

15. A spectrometer according to claim 14 wherein the thickness is equal to about 1 mm.

16. A spectrometer according to claim 12 wherein the support plate has a characteristic lateral dimension between about 16 mm and 24 mm.

17. A spectrometer according to claim 16 wherein the lateral dimension is equal to 20 mm.

18. A spectrometer according to claim 12 wherein the support plate is formed in the shape of a disc.

19. A spectrometer according to claim 1 wherein the controller controls intensity of light in the light pulses so that from pulse to pulse, intensity varies less than a predetermined amount from a normative intensity.

20. A spectrometer according to claim 19 wherein the pulse to pulse variance is less than about 10%.

21. A method of assaying a solid or liquid material, the method comprising:

illuminating a sample of the material with pulses of light at a plurality of different wavelengths at which atoms and/or molecules in the material are ionized in a multiphoton ionization (MPI) process;

measuring a value corresponding to charges produced in the ionization process for each wavelength to acquire an MPI spectrum for the material; and assaying an atom or molecule in the material based on the MPI spectrum.

22. A method according to claim 21 and configuring a light pulse so that it comprises light at wavelengths tuned to ionize an atom or molecule that might be present in the sample by the MPI process by causing transitions between particular energy states of the atom or molecule.

23. A method according to claim 22 and configuring a light pulse so that it comprises light at a first wavelength chosen to excite an electron of the atom or molecule from a given first energy state to a given second, excited, energy state, and light at a second wavelength chosen to add a given amount of energy to the excited electron to free it from the molecule.

24. A method according to claim 23 and choosing the second wavelength so that the light at the second wavelength adds a minimum amount of energy needed to free the electron from the second, excited, state and ionize the molecule.

25. A method according to claim 21 and controlling intensity of light in the light pulses so that from pulse to pulse, intensity varies less than a predetermined amount from a normative intensity.

26. A method according to claim 25 wherein the pulse to pulse variance is less than about 10%.

27. A method according to claim 21 and supporting the sample on insulating support plate.

28. A method according to claim 27 and forming the support plate from quartz.

29. A method according to claim 27 wherein the support plate has a thickness between about 0.5 mm and about 1.5 mm.

30. A method according to claim 27 wherein the support plate has a characteristic lateral dimension between about 16 mm and 24 mm.

31. A method according to claim 21 wherein the sample is maintained under ambient atmospheric conditions of temperature and pressure.

* * * * *